United States Patent
Yang et al.

(10) Patent No.: US 11,439,656 B2
(45) Date of Patent: Sep. 13, 2022

(54) PHARMACEUTICAL COMPOUNDS AND USES THEREOF

(71) Applicant: Regents of the University of Minnesota, Minneapolis, MN (US)

(72) Inventors: DaQing Yang, Austin, MN (US); Carston R. Wagner, St. Paul, MN (US); Aniekan Okon, Boston, MA (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 16/556,690

(22) Filed: Aug. 30, 2019

(65) Prior Publication Data
US 2020/0069712 A1 Mar. 5, 2020

Related U.S. Application Data

(60) Provisional application No. 62/725,223, filed on Aug. 30, 2018.

(51) Int. Cl.

| | | |
|---|---|---|
| *A01N 43/04* | (2006.01) | |
| *A61K 31/70* | (2006.01) | |
| *A61K 31/708* | (2006.01) | |
| *C07H 17/02* | (2006.01) | |
| *A61K 31/426* | (2006.01) | |
| *A61K 31/365* | (2006.01) | |
| *A61K 47/68* | (2017.01) | |
| *A61P 35/00* | (2006.01) | |
| *A61K 31/675* | (2006.01) | |
| *A61K 31/196* | (2006.01) | |
| *A61K 31/197* | (2006.01) | |
| *A61K 31/175* | (2006.01) | |

(Continued)

(52) U.S. Cl.
CPC .......... *A61K 31/708* (2013.01); *A61K 31/175* (2013.01); *A61K 31/196* (2013.01); *A61K 31/197* (2013.01); *A61K 31/365* (2013.01); *A61K 31/366* (2013.01); *A61K 31/426* (2013.01); *A61K 31/495* (2013.01); *A61K 31/675* (2013.01); *A61K 47/6809* (2017.08); *A61P 35/00* (2018.01); *C07H 17/02* (2013.01)

(58) Field of Classification Search
CPC ..... A61P 35/00; A61K 31/175; A61K 31/197; A61K 31/426; A61K 47/6809; A61K 31/365; A61K 31/495; A61K 31/708; A61K 31/196; A61K 31/366; A61K 31/675; C07H 17/02
See application file for complete search history.

(56) References Cited

U.S. PATENT DOCUMENTS

| | | | |
|---|---|---|---|
| 8,399,428 B2 * | 3/2013 | Wagner | A61P 35/00 |
| | | | 514/48 |
| 8,765,935 B2 * | 7/2014 | Wagner | C07H 19/167 |
| | | | 536/26.1 |

(Continued)

FOREIGN PATENT DOCUMENTS

WO WO-2016098028 A1 * 6/2016 .......... C07F 9/65616

OTHER PUBLICATIONS

Okon et al., "Anchimerically Activated Protides as Inhibitors of Cap-Dependent Translation and Inducers of Chemosensitization in Mantle Cell Lymphoma," Journal of Medicinal Chemistry, 60, 8131-8144 (2017).*

(Continued)

*Primary Examiner* — Patrick T Lewis
(74) *Attorney, Agent, or Firm* — Schwegman Lundberg & Woessner, P.A.

(57) ABSTRACT

Described herein are small molecule cap-dependent inhibitors, including the compound of the formula:

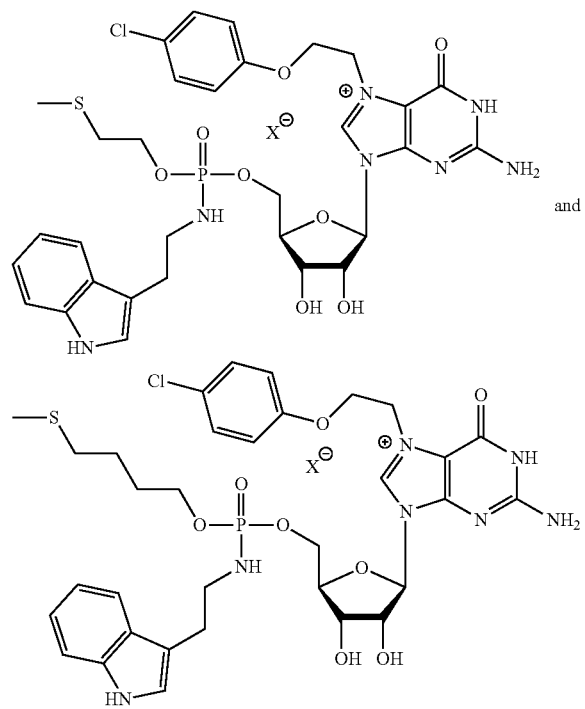

which compounds that can induce the accumulation of the p53 tumor suppressor protein in cancer cells that still express wild-type p53, as well as methods of using those (Continued)

compounds to, among other things, treat neuroblastoma, pediatric glioblastoma multiforme or breast cancer.

7 Claims, 6 Drawing Sheets

(51) Int. Cl.
*A61K 31/495* (2006.01)
*A61K 31/366* (2006.01)

(56) References Cited

U.S. PATENT DOCUMENTS

| | | | |
|---|---|---|---|
| 8,815,830 B2 * | 8/2014 | Wagner | C07H 19/052 514/51 |
| 10,676,499 B2 * | 6/2020 | Barnes-Seeman | C07H 19/167 |

OTHER PUBLICATIONS

Kore et al., "Synthesis and Biological Validation of N7-(4-chlorophenoxyethyl)substituted Dinucleotide Cap Analogs for mRNA Translation," Bioorganic and Medicinal Chemistry, 21, 4570-4574 (2013).*

Guimaraes et al., "Thermodynamic Analysis of mRNA Cap Binding by the Human Initiation Factor eIFE4 via Free Energy Perturbations," Journal of the American Chemical Society, 131(50), 18139-18146 (2009).*

* cited by examiner

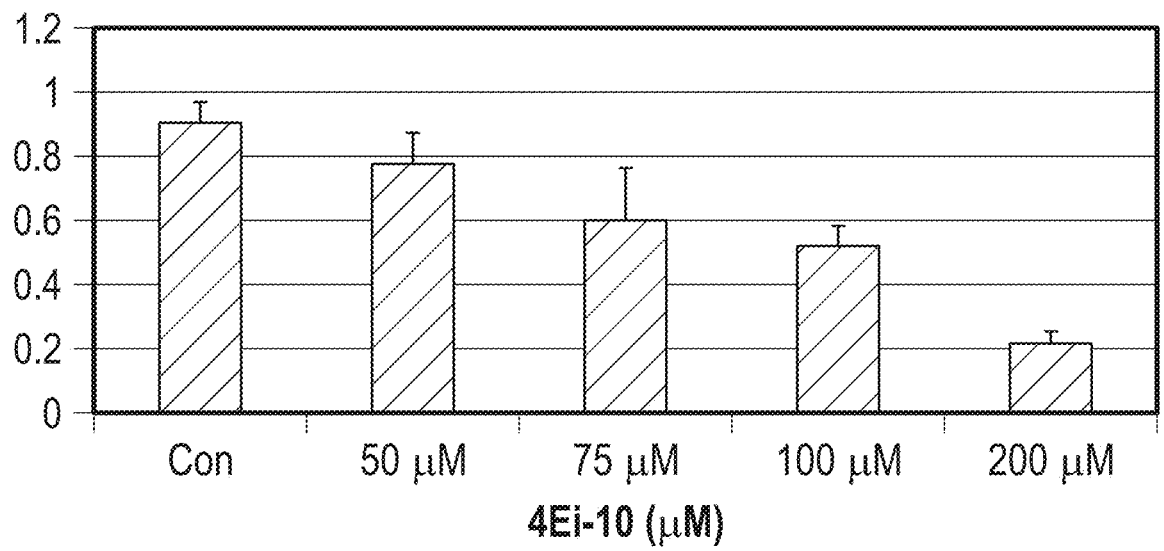
FIG. 1B
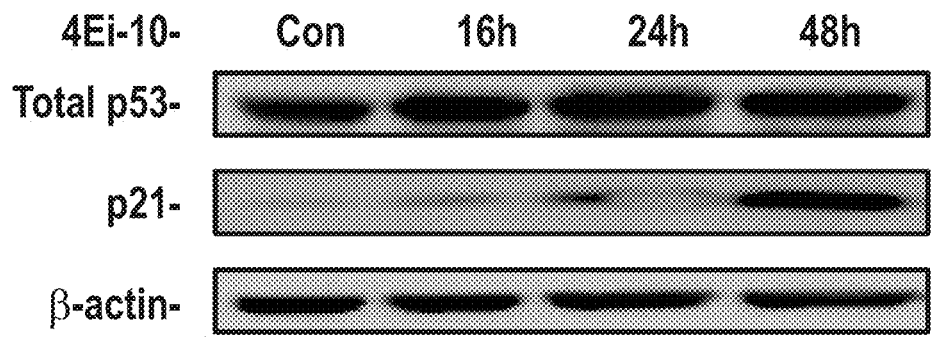
FIG. 1C
| SH-SY5Y | G1 | S | G1/S* |
|---|---|---|---|
| Control | 68.44 | 17.23 | 4.0 |
| 4Ei-10 | 75.96 | 9.17 | 8.3 |
FIG. 1D

PHARMACEUTICAL COMPOUNDS AND USES THEREOF

CROSS-REFERENCE TO RELATED APPLICATIONS

This application claims the benefit of U.S. Provisional Appl. Ser. No. 62/725,223 filed Aug. 30, 2018, which is incorporated as if set forth herein in its entirety.

This invention was made with government support under CA177954 awarded by the National Institutes of Health. The government has certain rights in the invention.

BACKGROUND

Protein synthesis is the most energy-consuming process in the cell. It is heavily regulated by multiple protein translation factors that predominantly affect the initiation step. In cancer cells, protein translation is deregulated, allowing cells to continuously move through the cell cycle without stopping at the proper checkpoints. Because of this, multiple signaling pathways and proteins that regulate protein translation have been identified as potential therapeutic targets. One such target that has received great attention is eukaryotic initiation factor 4E (eIF4E).

mRNAs in eukaryotic organisms are typically translated in a cap-dependent manner because the majority of them contain a cap structure, m7GpppN (where N is any nucleotide), at their 5'-terminus. The initial and rate limiting step of translation initiation is the recognition and the binding of this cap structure by eIF4E. eIF4E then recruits and binds to eIF4G and eIF4A to assemble the eIF4F translation initiation complex, which facilitates the cap-dependent protein translation of eukaryotic mRNAs.

It is known that the activity of eIF4E and cap-dependent protein translation is elevated in cancer cells and the overexpression and hyperactivation of eIF4E cause malignant transformation and metastasis in many different types of cancers. Multiple lines of evidence suggest that inhibition of eIF4E results in stalled tumor growth and repressed metastasis without substantially affecting normal cellular and organismal function. Therefore, eIF4E has become a promising target for cancer therapy. Cap-dependent protein translation is inhibited by eIF4E binding proteins (4E-BPs), including 4E-BP1. When 4E-BP1 is hypophosphorylated, it competes with eIF4G for binding to eIF4E. Once 4E-BP1 is bound to eIF4E, it inhibits cap-dependent protein translation by preventing the formation of the eIF4F complex. Recent studies have shown that inhibiting eIF4E function in cancer cells leads to cell growth arrest and apoptosis, however the underlying mechanism for induction of these events through inhibition of cap-dependent protein translation is unclear.

During stressful conditions such as DNA damage, an alternative mode of translation, termed cap-independent translation, occurs by utilizing the internal ribosomal entry sites (IRES) in the 5'-untranslated regions (5'-UTRs) of mRNAs rather than eIF4E. An IRES sequence within the 5'-UTR of p53 mRNA has been discovered. It was also found that p53 IRES activity increases following DNA damage. The p53 tumor suppressor plays a key role in response to DNA damage or other cellular stress by halting cell cycle progression or inducing apoptosis. Under normal conditions, p53 levels are low, as p53 is induced only after DNA damage or other cellular stress. While it was thought that p53 induction is regulated through post-translational modifications which inhibit MDM2 from binding it for degradation, leading to increased half-life of p53, it is now clear that the p53 IRES-mediated translation of p53 mRNA also contributes to the accumulation of p53 following DNA damage and other stress signals.

While p53 is the most commonly mutated gene in cancer, p53 mutation rates are much lower in certain types of cancer, including the majority of pediatric cancers (1-19%) such as neuroblasoma and adult cancers such as breast and prostate cancer. Searching for small molecules that can reactivate p53 tumor suppressor in cancer cells that retain wild-type p53 has been an intensive area of research. It was discovered that a switch from cap-dependent protein translation to IRES-mediated translation of p53 mRNA following DNA damage, which is accompanied by an increase of 4E-BP1 bound to eIF4E. Others have made similar findings in which a transition from cap-dependent protein translation to IRES-mediated synthesis of the p53 protein occurs in response to not only DNA damage but also other cellular stress, such as oncogene-induced senescence. Based on these observations, we hypothesized that halting cap-dependent protein translation in cancer cells by inhibiting eIF4E function would mimic conditions of DNA damage and cause IRES-mediated translation of p53 mRNA, leading to cell cycle arrest and apoptosis.

DESCRIPTION OF THE FIGURES

The drawings illustrate generally, by way of example, but not by way of limitation, various embodiments discussed in the present document.

FIG. 1B shows inhibition of SH-SY5Y (a neuroblastorna cell line with wild-type p53) proliferation by different concentrations of 4Ei-10.

FIG. 1C is an immunoblot showing p53 and p21Cip1 induction by 4Ei-10 in SH-SY5Y cells.

FIG. 1D is a table showing the cell cycle distribution in G1, S, and G1/S ratio of SH-SY5Y cells treated with or without 4Ei-10.

SUMMARY

Figure 1A:
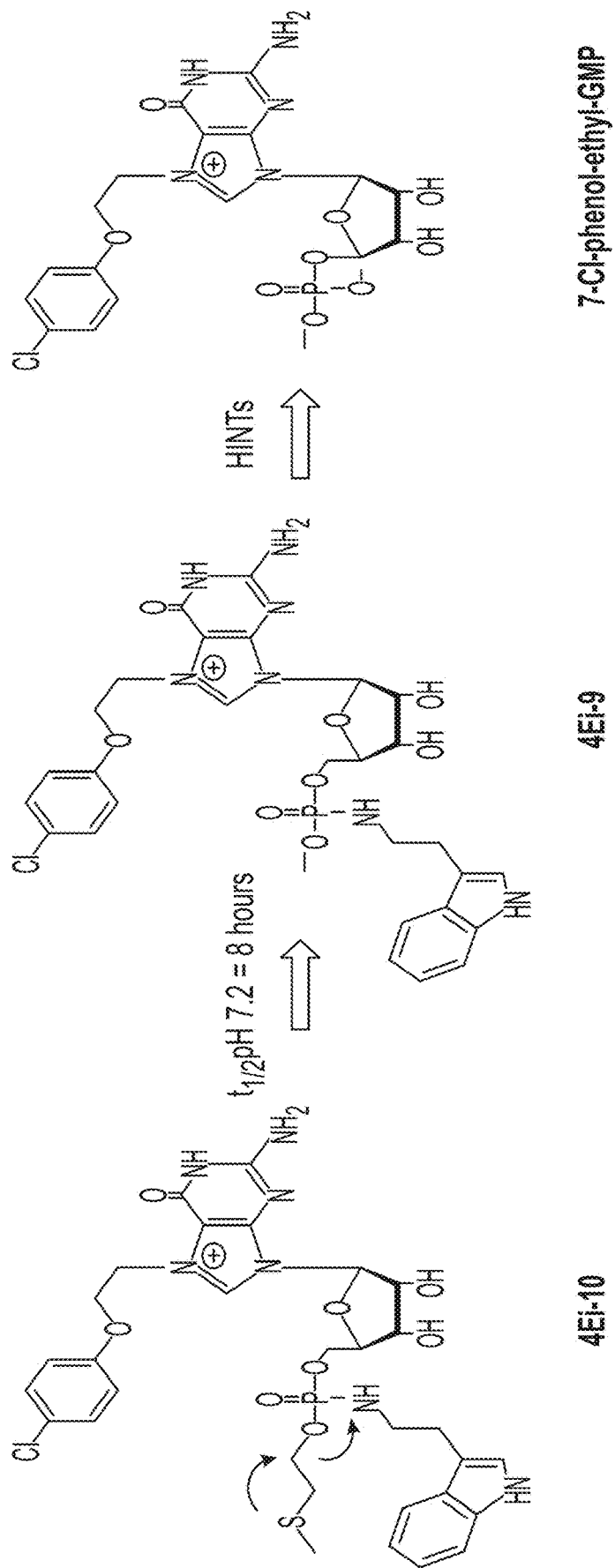
FIG. 1A is a scheme showing a proposed mechanism for "4Ei-10" intracellular release of "7Cl-Ph-Ethyl-GMP."

The instant disclosure generally relates to small molecule cap-dependent inhibitors that can induce the accumulation of the p53 tumor suppressor protein in cancer cells that still express wild-type p53.

An example of a small molecule inhibitor is the compound referred to herein as "4Ei-10," which is able to induce the accumulation of the p53 tumor suppressor protein in cancer cells that still express wild-type p53.

"4Ei-10"

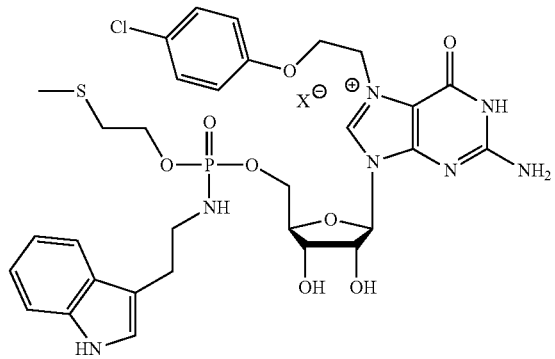

wherein X⁻ represents a counterion.

The results described herein show that 4Ei-10 causes an increase in IRES activity of p53 mRNA, leading to increased accumulation of the p53 tumor suppressor protein without inducing DNA double strand breaks. It was also found that 4Ei-10 inhibits cancer cell proliferation by inducing cell cycle arrest and cell apoptosis.

DESCRIPTION

Reference will now be made in detail to certain examples of the disclosed subject matter. While the disclosed subject matter will be described in conjunction with the enumerated claims, it will be understood that the exemplified subject matter is not intended to limit the claims to the disclosed subject matter.

The instant disclosure generally relates to small molecule cap-dependent inhibitors that can induce the accumulation of the p53 tumor suppressor protein in cancer cells that still express wild-type p53. These small molecule inhibitors have the general formula (I):

(I)

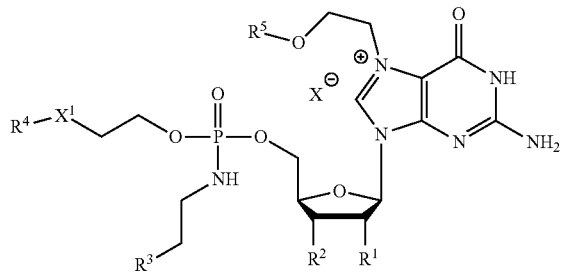

or a pharmaceutically acceptable salt, solvate or prodrug thereof;
wherein:
X⁻ represents a counterion.
$R^1$ and $R^2$ are each independently H, OH or alkoxy;
$R^3$ is alkyl, aryl or heterocyclyl;
$R^4$ is alkyl or aryl;
$R^5$ is aryl; and
$X^1$ is NH, S or O.

The compound of the formula (I) can also be a compound of the formula (II):

(II)

or a pharmaceutically acceptable salt, solvate or prodrug thereof;
wherein:
$X^1$ represents a counterion.
$R^1$ and $R^2$ are each independently H, OH or alkoxy;
$R^4$ is alkyl or aryl;
$R^5$ is aryl;
$X^1$ and $X^2$ are each independently NH, S or O;
$R^6$ and $R^7$ can each independently be H, alkyl, aryl or $R^6$ and $R^7$, together with the carbon atoms to which they are attached, can form an aryl group.

A compound that falls within the scope of the formulae (I) and (II) is the compound of formula (III):

(III)

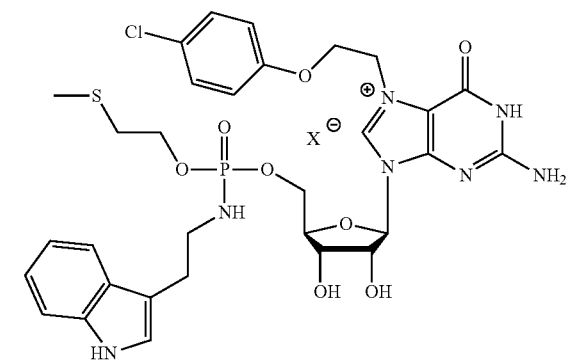

or a pharmaceutically acceptable salt, solvate or prodrug thereof, wherein X⁻ represents a counterion. The compound of the formula (III) is also referred to herein as "4Ei-10."

The instant disclosure also relates to a compound of the formula:

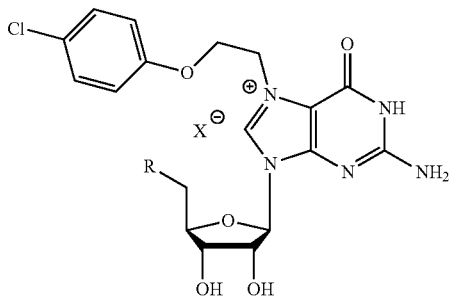

or a pharmaceutically acceptable salt, solvate or prodrug thereof, wherein X⁻ represents a counterion, R represents nucleotidomimetic derivatives of the substituted phosphate group, of (III) and the phosphate group of (IIIb), such as sulfamides, sulfamates, sulfonamides, carboxylic acids, and tetrazole analogs, etc., thereof. The compound of the formula (III) is also referred to herein as "4Ei-10."

The instant disclosure also relates to a compound of the formula (IIIa) and (IIIb):

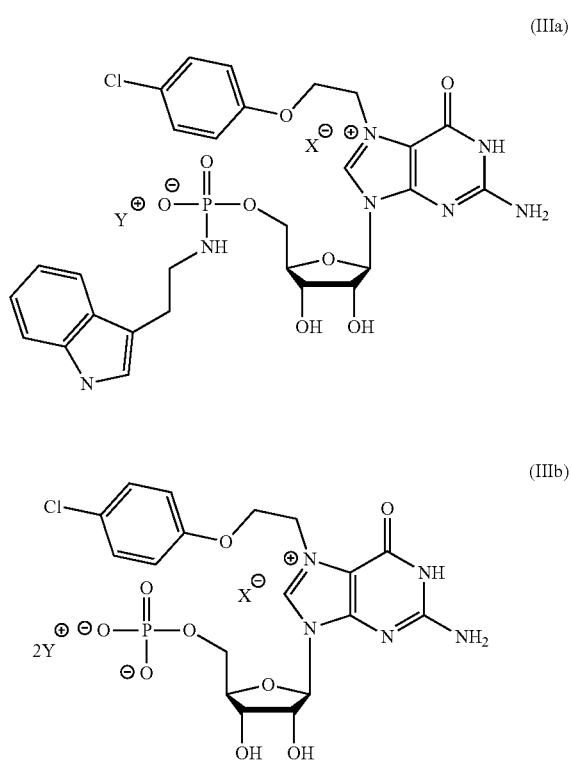

or a pharmaceutically acceptable salt, solvate or prodrug thereof, wherein X⁻ and Y⁺ represent counterions. The compounds of the formula (IIIa) and (IIIb) are formed from the compound of the formula (III) as shown in FIG. 1A. Accordingly, the instant disclosure contemplates any compound that forms the compound of formula (IIIb) in vivo, such as a compound of the formula (I)-(III), and its use according to the methods described herein.

The compounds of formula (I), (II), (III), (IIIa) and/or (IIIb) can be used generally in methods for treating cancer comprising administering a therapeutically effective amount of a compound of formula (I), (II), (III), (IIIa) and/or (IIIb) to a subject, such as a mammal (e.g., a human), in need thereof. Examples of cancers that can be treated with the compound of formula (I), (II), (III), (IIIa) and/or (IIIb) include all the cancers that retain wild-type p53. More specifically, the compound of the formula (I), (II), (III), (IIIa) and/or (IIIb) can be used to treat neuroblastoma, pediatric glioblastoma multiforme, breast cancer, prostate cancer or mantle cell lymphoma.

The compound of the formula (I), (II), (III), (IIIa) and/or (IIIb) can be used in a method for inducing cell-cycle arrest and apoptosis in a subject, the method comprising administering an amount of a compound of f formula (I), (II), (III), (IIIa) and/or (IIIb) to the subject sufficient to induce cell-cycle arrest and apoptosis in the subject.

The compound of the formula (I), (II), (III), (IIIa) and/or (IIIb)) can be used in a method for inhibiting cap-dependent protein translation in a subject, the method comprising administering an amount of a compound of formula (I), (II), (III), (IIIa) and/or (IIIb) to the subject sufficient to inhibit cap-dependent protein translation in the subject.

The compound of the formula (I), (II), (III), (IIIa) and/or (IIIb) can be used in a method for increasing IRES activity of p53 mRNA in a subject, the method comprising administering an amount of a compound of formula (I), (II), (III), (IIIa) and/or (IIIb) to the subject sufficient to increase IRES activity of p53 mRNA in the subject.

The compound of the formula (I), (II), (III), (IIIa) and/or (IIIb) can be used in a method for inducing the accumulation of the p53 tumor suppressor protein in cancer cells retaining wild-type p53 in a subject, the method comprising administering an amount of a compound of formula (I), (II), (III), (IIIa) and/or (IIIb) to the subject sufficient to induce the accumulation of the p53 tumor suppressor protein in cancer cells retaining wild-type p53 in the subject.

In any one of the aforementioned methods, the inducing cell-cycle arrest and apoptosis, inhibiting cap-dependent protein translation, increasing internal ribosomal entry site activity or the inducing the accumulation of the p53 tumor suppressor protein in cancer cells retaining wild-type p53, respectively, occurs without inducing DNA damage. As used herein, the term "without inducing DNA damage" generally means no detectable DNA damage relative to a known DNA damaging agent. DNA damage includes DNA double strand breaks, DNA single strand breaks, intercalation or nicking of the DNA backbone, etc.

In any of the aforementioned methods, the compound of the formula (I), (II), (III), (IIIa) and/or (IIIb) can be administered either alone or in combination with another chemotherapeutic agent and/or in combination with radiation therapy. For example, the compound of the formula (I), (II), (III), (IIIa) and/or (IIIb) can be administered in combination with one or more DNA damaging chemotherapeutic or radiation therapeutic agents. Examples, of DNA damaging is chemotherapeutic agents include etoposide, doxorubicin, camptothecin, cyclophosphamide, chlorambucil, melphalan, carmustine, lomustine, semustine, decarbazine, and temozolomide, etc., or in general any chemotherapeutic agents.

In any of the aforementioned methods, the compound of formula (I), (II), (III), (IIIa) and/or (IIIb) can be administered in combination with a compound of the formula (IV):

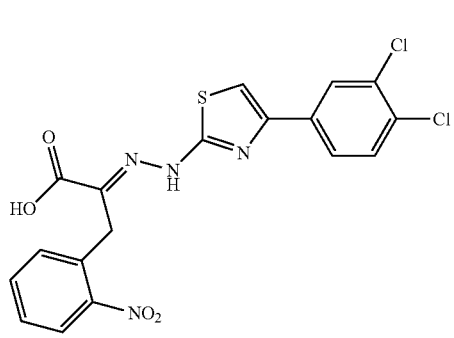

(IV)

or a pharmaceutically acceptable salt, solvate or prodrug thereof.

The term "alkyl" as used herein refers to substituted or unsubstituted straight chain, branched and cyclic, saturated mono-valent groups having from 1 to 20 carbon atoms, 10 to 20 carbon atoms, 12 to 18 carbon atoms, 6 to about 10 carbon atoms, 1 to 10 carbons atoms, 1 to 8 carbon atoms, 2 to 8 carbon atoms, 3 to 8 carbon atoms, 4 to 8 carbon atoms, 5 to 8 carbon atoms, 1 to 6 carbon atoms, 2 to 6 carbon atoms, 3 to 6 carbon atoms, or 1 to 3 carbon atoms. Examples of straight chain mono-valent $(C_1-C_{20})$-alkyl groups include those with from 1 to 8 carbon atoms such as methyl (i.e., $CH_3$), ethyl, n-propyl, n-butyl, n-pentyl, n-hexyl, n-heptyl, n-octyl groups. Examples of branched mono-valent $(C_1-C_{20})$-alkyl groups include isopropyl, isobutyl, sec-butyl, t-butyl, neopentyl, and isopentyl. Examples of cyclic alkyl groups include cyclopropyl, cyclobutyl, cyclopently, cyclohexyl, cyclooctyl, bicyclo[1.1.1]pentyl, bicyclo[2.1.1]hexyl, and bicyclo[2.2.1]heptyl. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Alkyl includes a combination of substituted and unsubstituted alkyl. As an example, alkyl, and also $(C_1)$alkyl, includes methyl and substituted methyl. As a particular example, $(C_1)$alkyl includes benzyl. As a further example, alkyl can include methyl and substituted $(C_2-C_8)$alkyl. Alkyl can also include substituted methyl and unsubstituted $(C_2-C_8)$alkyl. Alkyl can be methyl and $C_2-C_8$ linear alkyl. Alkyl can be methyl and $C_2-C_8$ branched alkyl. The term methyl is understood to be —$CH_3$, which is not substituted. For comparison, the term $(C_1)$alkyl is understood to be a substituted or an unsubstituted —$CH_3$. Representative substituted alkyl groups can be substituted one or more times with any of the groups listed herein, for example, cycloalkyl, heterocyclyl, aryl, amino, haloalkyl, hydroxy, cyano, carboxy, nitro, thio, alkoxy, and halogen groups. As further example, representative substituted alkyl groups can be substituted one or more fluor, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. The term "alkyl" also generally refers to alkyl groups that can comprise one or more heteroatoms in the carbon chain. Thus, for example, "alkyl" also encompasses groups such as —[$(CH_2)_pO]_qH$ and the like.

The term "aryl" as used herein refers to substituted or unsubstituted univalent groups that are derived by removing a hydrogen atom from an arene, which is a cyclic aromatic hydrocarbon, having from 6 to 20 carbon atoms, 10 to 20 carbon atoms, 12 to 20 carbon atoms, 6 to about 10 carbon atoms or 6 to 8 carbon atoms. Examples of $(C_6-C_{20})$aryl groups include phenyl, napthalenyl, azulenyl, biphenylyl, indacenyl, fluorenyl, phenanthrenyl, triphenylenyl, pyrenyl, naphthacenyl, chrysenyl, anthracenyl groups. Examples include substituted phenyl, substituted napthalenyl, substituted azulenyl, substituted biphenylyl, substituted indacenyl, substituted fluorenyl, substituted phenanthrenyl, substituted triphenylenyl, substituted pyrenyl, substituted naphthacenyl, substituted chrysenyl, and substituted anthracenyl groups. Examples also include unsubstituted phenyl, unsubstituted napthalenyl, unsubstituted azulenyl, unsubstituted biphenylyl, unsubstituted indacenyl, unsubstituted fluorenyl, unsubstituted phenanthrenyl, unsubstituted triphenylenyl, unsubstituted pyrenyl, unsubstituted naphthacenyl, unsubstituted chrysenyl, and unsubstituted anthracenyl groups. From these examples, it is clear that the term $(C_6-C_{20})$aryl encompasses mono- and polycyclic $(C_6-C_{20})$aryl groups, including fused and non-fused polycyclic $(C_6-C_{20})$aryl groups.

The term "heterocyclyl" as used herein refers to substituted aromatic, unsubstituted aromatic, substituted non-aromatic, and unsubstituted non-aromatic rings containing 3 or more atoms in the ring, of which, one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms $(C_3-C_6)$, 3 to 6 carbon atoms $(C_3-C_6)$ or 6 to 8 carbon atoms $(C_6-C_8)$. A heterocyclyl group designated as a $C_2$-heterocyclyl can be a 5-membered ring with two carbon atoms and three heteroatoms, a 6-membered ring with two carbon atoms and four heteroatoms and so forth. Likewise a $C_4$-heterocyclyl can be a 5-membered ring with one heteroatom, a 6-membered ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to piperidynyl, piperazinyl, morpholinyl, furanyl, pyrrolidinyl, pyridinyl, pyrazinyl, pyrimidinyl, triazinyl, thiophenyl, tetrahydrofuranyl, pyrrolyl, oxazolyl, imidazolyl, triazyolyl, tetrazolyl, indolyl, benzoxazolinyl, and benzimidazolinyl groups. For example, heterocyclyl groups include, without limitation:

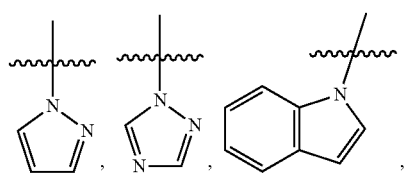

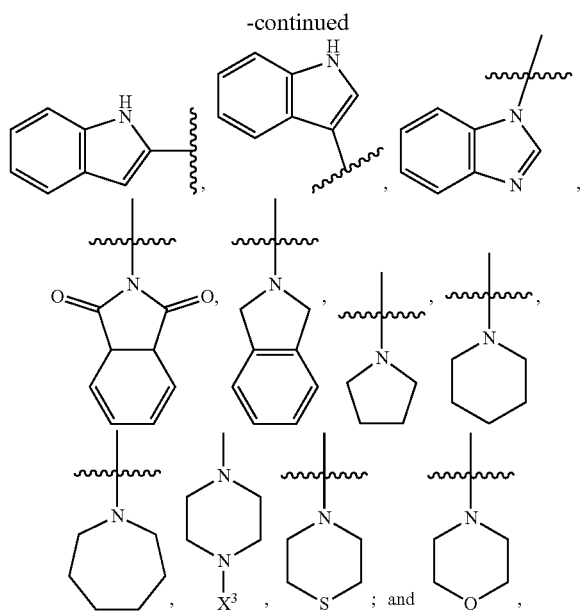

wherein $X^3$ represents H, $(C_1\text{-}C_{20})$alkyl, $(C_6\text{-}C_{20})$aryl or an amine protecting group (e.g., a t-butyloxycarbonyl group) and wherein the heterocyclyl group can be substituted or unsubstituted. A nitrogen-containing heterocyclyl group is a heterocyclyl group containing a nitrogen atom as an atom in the ring. In some embodiments, the heterocyclyl is other than thiophene or substituted thiophene. In some embodiments, the heterocyclyl is other than furan or substituted furan.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. Thus, alkyoxy also includes an oxygen atom connected to an alkyenyl group and oxygen atom connected to an alkynyl group. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The terms "halo," "halogen," or "halide" group, as used herein, by themselves or as part of another substituent, mean, unless otherwise stated, a fluorine, chlorine, bromine, or iodine atom.

The term "substituted" as used herein refers to a group that is substituted with one or more groups including, but not limited to, the following groups: halogen (e.g., F, Cl, Br, and I), R, OR, OC(O)N(R)$_2$, CN, NO, NO$_2$, ONO$_2$, azido, CF$_3$, OCF$_3$, methylenedioxy, ethylenedioxy, $(C_3\text{-}C_{20})$heteroaryl, N(R)$_2$, Si(R)$_3$, SR, SOR, SO$_2$R, SO$_2$N(R)$_2$, SO$_3$R, P(O)(OR)$_2$, OP(O)(OR)$_2$, C(O)R, C(O)C(O)R, C(O)CH$_2$C(O)R, C(S)R, C(O)OR, OC(O)R, C(O)N(R)$_2$, C(O)N(R)OH, OC(O)N(R)$_2$, C(S)N(R)$_2$, (CH$_2$)$_{0\text{-}2}$N(R)C(O)R, (CH$_2$)$_{0\text{-}2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R wherein R can be hydrogen, $(C_1\text{-}C_{20})$alkyl or $(C_6\text{-}C_{20})$aryl. Substituted also includes a group that is substituted with one or more groups including, but not limited to, the following groups: fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. Where there are two or more adjacent substituents, the substituents can be linked to form a carbocyclic or heterocyclic is ring. Such adjacent groups can have a vicinal or germinal relationship, or they can be adjacent on a ring in, e.g., an ortho-arrangement. Each instance of substituted is understood to be independent. For example, a substituted aryl can be substituted with bromo and a substituted heterocycle on the same compound can be substituted with alkyl. It is envisaged that a substituted group can be substituted with one or more non-fluoro groups. As another example, a substituted group can be substituted with one or more non-cyano groups. As another example, a substituted group can be substituted with one or more groups other than haloalkyl. As yet another example, a substituted group can be substituted with one or more groups other than tert-butyl. As yet a further example, a substituted group can be substituted with one or more groups other than trifluoromethyl. As yet even further examples, a substituted group can be substituted with one or more groups other than nitro, other than methyl, other than methoxymethyl, other than dialkylaminosulfonyl, other than bromo, other than chloro, other than amido, other than halo, other than benzodioxepinyl, other than polycyclic heterocyclyl, other than polycyclic substituted aryl, other than methoxycarbonyl, other than alkoxycarbonyl, other than thiophenyl, or other than nitrophenyl, or groups meeting a combination of such descriptions. Further, substituted is also understood to include fluoro, cyano, haloalkyl, tert-butyl, trifluoromethyl, nitro, methyl, methoxymethyl, dialkylaminosulfonyl, bromo, chloro, amido, halo, benzodioxepinyl, polycyclic heterocyclyl, polycyclic substituted aryl, methoxycarbonyl, alkoxycarbonyl, thiophenyl, and nitrophenyl groups.

This disclosure also contemplates pharmaceutical compositions comprising a compound of the formula (I), (II), (III), (IIIa) and/or (IIIb), or a pharmaceutically acceptable salt, solvate or prodrug thereof, optionally in combination with a compound of formula (IV) or a pharmaceutically acceptable salt, solvate or prodrug thereof, and one or more pharmaceutically acceptable carriers, diluents, excipients or combinations thereof. A "pharmaceutical composition" refers to a chemical or biological composition suitable for administration to a subject (e.g., mammal). Such compositions may be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In is addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington. The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. In one example, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions may be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be is brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions of the present invention may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions of the present invention may include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited examples, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multilayer tablets, hi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets is or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various examples of the present invention may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds of the present invention or an appropriate pharmaceutical composition thereof are effective, the is compounds of the present invention may be administered in an effective amount. The dosages as suitable for this invention may be a composition, a pharmaceutical composition or any other compositions described herein.

For each of the recited examples, the dosage is typically administered once, twice, or thrice a day, although more frequent dosing intervals are possible. The dosage may be administered every day, every 2 days, every 3 days, every 4 days, every 5 days, every 6 days, and/or every 7 days (once a week). In one example, the dosage may be administered daily for up to and including 30 days, preferably between 7-10 days. In another example, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, the composition of this invention may be to effect prophylaxis of recurring symptoms. For example, the dosage may be administered once or twice a day to prevent the onset of symptoms in patients at risk, especially for asymptomatic patients.

The compositions described herein may be administered in any of the following routes; buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

This disclosure also contemplates pharmaceutical compositions comprising a compound of the formula (I), (Ia) or (Ib), or a pharmaceutically is acceptable salt, solvate or prodrug thereof, optionally in combination with a compound of formula (II) or a pharmaceutically acceptable salt, solvate or prodrug thereof, for use as a medicament for treating a patient in need of relief from a disease or a condition, such as cancer.

The term "therapeutically effective amount" as used herein, refers to that amount of one or more compounds of the various examples of the present invention that elicits a biological or medicinal response in a tissue system, animal or human, that is being sought by a researcher, veterinarian, medical doctor or other clinician, which includes alleviation of the symptoms of the disease or disorder being treated. In some examples, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient; the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfanilic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001 Wiley) and Design and Application of Prodrugs (H. Bundgaard ed., 1985, Harwood Academic Publishers GmbH).

EXAMPLES

The present invention can be better understood by reference to the following examples which are offered by way of illustration. The present invention is not limited to the examples given herein.

Materials and Methods

Chemicals and reagents: 4Ei-10 was synthesized by Dr. Garston Wagner's laboratory at the University of Minnesota. 4EGI-1 was purchased from Millipore and has the following structure:

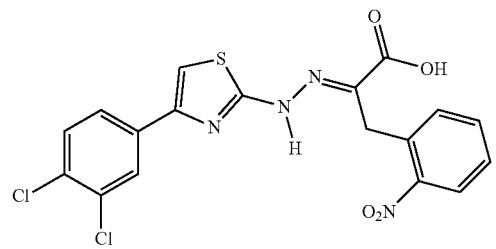 [SMILES: O=C(O)/C(Cc1ccccc1[N+](=O)[O-])=N/Nc1nc(-c2ccc(Cl)c(Cl)c2)cs1]

The antibody against human p53 tumor suppressor protein was purchased from Santa Cruz. The antibody against phosphor-H2A.X was purchased from Millipore. The antibodies against poly ADP-ribose polymerase (PARP), and p21Cip1 were from Cell Signaling Technologies.

Cell culture, cell extract preparation, SDS-PAGE, and western blot: SH-SY5Y pediatric neuroblastoma cells were purchased from ATCC. Pediatric glioblastoma multiforme cell line CHLA-200 was a generous gift from Dr. C. Patrick Reynolds (Texas Tech). Cancer cells were cultured in RPMI-1640 supplemented with 10% fetal bovine serum (FBS) and 1% Penicillin-Streptomycin. Cells were lysed with RIPA lysis buffer (Millipore) containing protease inhibitor cocktails (Roche). The protein concentration was measured by the Lowry method. Equal amounts of protein were subjected to SDS-PAGE and then transferred to a PVDF membrane. The proteins of interest were then probed with their respective antibodies.

MTT cell viability assay: Cells were plated on a 24-well plate at 20,000 cells/well. After treatment with different reagents, the ratio of viable cells in each well was determined using a CellTiter Cell Proliferation kit (Promega) following the manufacturer's instructions. MTS solution was placed in each well at a ratio of 20 μL/100 μL of cell culture medium and incubated in a cell culture incubator for 2-3 hours. Absorbance was then measured at the wavelength of 492 nm with a microplate reader.

Flow Cytometry Assay of Cell Cycle Distribution: Cells were seeded onto six well plates and were grown to sub-confluency. After treatment with or without 4Ei-10, cells were gently removed from the plates, washed once with cold PBS, and fixed with cold 70% ethanol. Cells were then stained with propidium iodide and subjected to flow cytometry (Becton Dickinson FACScalibur). The cell population at each phase was analyzed by the Modfit 2 software.

Dual luciferase assays: Cells were lysed with passive lysis buffer (Promega). The dual-luciferase reporter assay (Promega) was then performed according to the manufacturer's instructions. Firefly and Renilla luciferase activities were determined with a Synergy 2 (BioTek) microplate reader.

Indirect immunofluorescence: Chamber slides (8 wells, Lab-Tek) were treated with Poly-L-Lysine (Sigma) prior to seeding with SH-SY5Y cells at 8000 cells/well. Sub-confluent cells were treated with different reagents. After treatment, cells were briefly fixed in 3% paraformaldehyde solution and were then permeablized with 0.2% Triton X-100 in Tris-buffered saline. After permeabilization, cells were incubated with a phosphor-Histone H2A.X antibody (Millipore) and then with a Texas-Red conjugated secondary antibody (Jackson Laboratories) followed by DAPI staining. Images were recorded using a Nikon Eclipse TE2000-E confocal microscope at 60× magnification.

Example 1

SH-SY5Y cells were treated with 4Ei-10. SH-SY5Y is a neuroblastoma cell line that contains wild-type p53. 4Ei-10 is a small molecule translation inhibitor. It is a prodrug that is converted to N7-chlorophenoxyethyl guanosine monophosphate by the enzyme hHINT1 in the cell as shown in FIG. 1A. N7-chlorophenoxyethyl guanosine monophosphate competes with the cap structure for binding to eIF-4E, preventing the recruitment of the 5' mRNA cap structure to the eIF-4F complex. It was found that 4Ei-10 caused a decrease in cell viability or cell proliferation in a concentration-dependent manner as shown in FIG. 1B. A time-course study was then performed by treating SH-SY5Y cells with 4Ei-10 at a concentration of 100 µM. It was found that 4Ei-10 not only induced p53 tumor suppressor protein accumulation but also caused increased expression of the p53 tumor suppressor protein downstream target p21Cip1 as shown in FIG. 1C.

Since the p53 tumor suppressor protein is known to induce cell cycle arrest through induction of p21Cip1, a cell cycle distribution analysis was performed after treating SH-SY5Y cells with 4Ei-10. Consistent with increased p21Cip1 induction, it was found that 4Ei-10 resulted in a substantial increase in cell numbers at the G1 phase and a dramatic decrease at the S phase in SH-SY5Y cells as shown in FIG. 1D. As compared to control cells, a two-fold increase in the G1S ratio, an indicator of G1 cell cycle arrest, was observed in SH-SY5Y cells treated with 4Ei-10 as shown in FIG. 1D.

Example 2

Figure 2A:
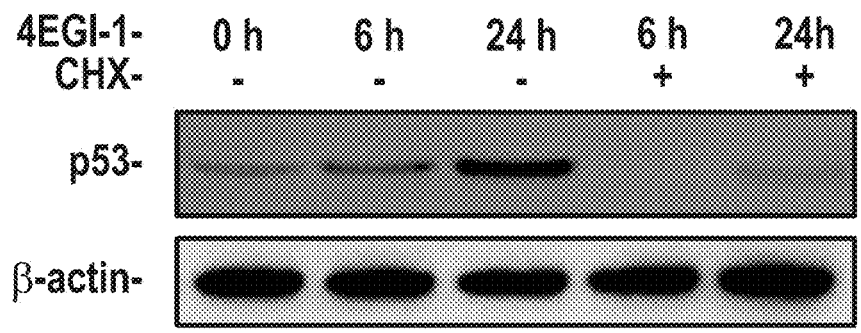
FIG. 2A is an immunoblot showing the accumulation of p53 induced by 4Ei-10 was blocked by a protein synthesis inhibitor.

To determine if the increase of the p53 tumor suppressor protein caused by 4Ei-10 is associated with enhanced p53 tumor suppressor protein synthesis, SH-SY5Y cells were treated with 4Ei-10 or 4Ei-10 plus cycloheximide, a protein synthesis (elongation) inhibitor. It was found that an induction of the p53 tumor suppressor protein following treatment of SH-SY5Y cells with 4Ei-10 as shown in FIG. 2A. However, this increased accumulation was abrogated when cells were treated with cycloheximide, suggesting that the induction of the p53 is tumor suppressor protein is caused by enhanced p53 tumor suppressor protein synthesis.

Example 3

Figure 2B:
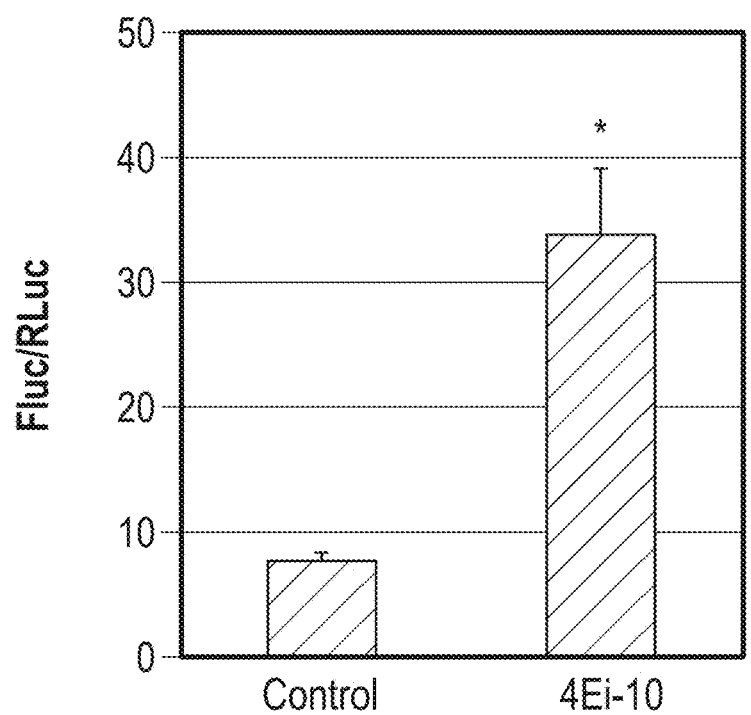
FIG. 2B shows the IRES activity (shown by the ratio of Fluc/Rluc) of p53 mRNA is increased after treating SH-SY5Y cells with 4Ei-10.

To determine if the IRES activity of p53 mRNA increases during 4Ei-10 treatment when cap-dependent protein translation is halted by 4Ei-10, a bicistronic dual-luciferase reporter vector pR5UTRF, which contains the IRES sequence (−131 nt before 1st AUG of p53 ORF, accession number, NM_00546.4) of the p53 mRNA, was used to transfect SH-SY5Y cells. The IRES activity of p53 mRNA was then measured as the ratio of firefly (Fluc, controlled by the IRES sequence of p53 mRNA) to Renilla luciferase (Rluc) activity, Rluc is controlled by eIF4E and cap-dependent protein translational machinery and was used as an internal control for Fluc. It was found that in SH-SY5Y cells transfected with pR5UTRF and treated with 4Ei-10, the IRES activity of p53 mRNA was significantly increased, shown by enhanced ratio of Fluc/Rluc following 4Ei-10 treatment, compared to untreated control cells as shown in FIG. 2B.

Example 4

Figure 3A:
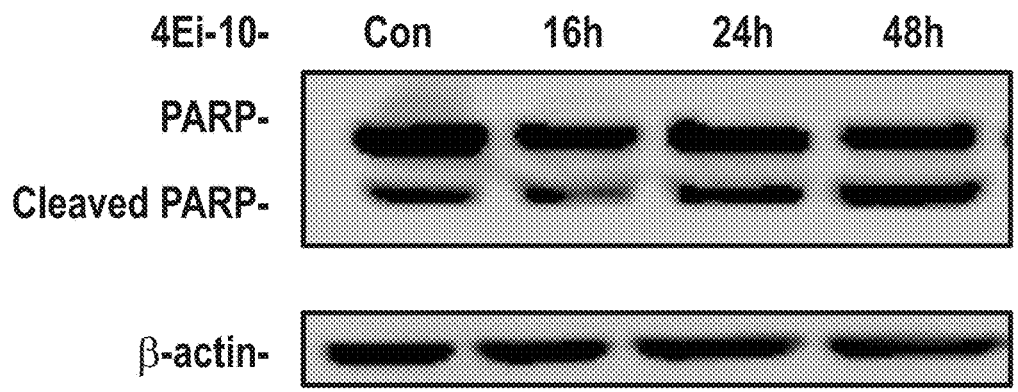
FIG. 3A is an immunoblot showing that 4Ei-10 induces apoptosis in SH-SY5Y cells after prolonged treatment.

Since the p53 tumor suppressor protein is also a stimulator of cell apoptosis, the levels of PARP, a substrate of caspase 3, were examined in SH-SY5Y cells treated with 4Ei-10. It was found that at a concentration of 100 µM, 4Ei-10 caused an increase of cleaved PARP, indicating enhanced cellular apoptosis, as shown in FIG. 3A. This was also shown by a Cell Death ELISA analysis, which further indicates that 4Ei-10 caused enhanced cell death or apoptosis of SH-SY5Y cells (data not shown). However, the apoptosis induced by 4Ei-10 was relatively weak and could be seen only after prolonged treatment (≥24 hours) of the cells as shown in FIG. 3A.

Example 5

Figure 3B:
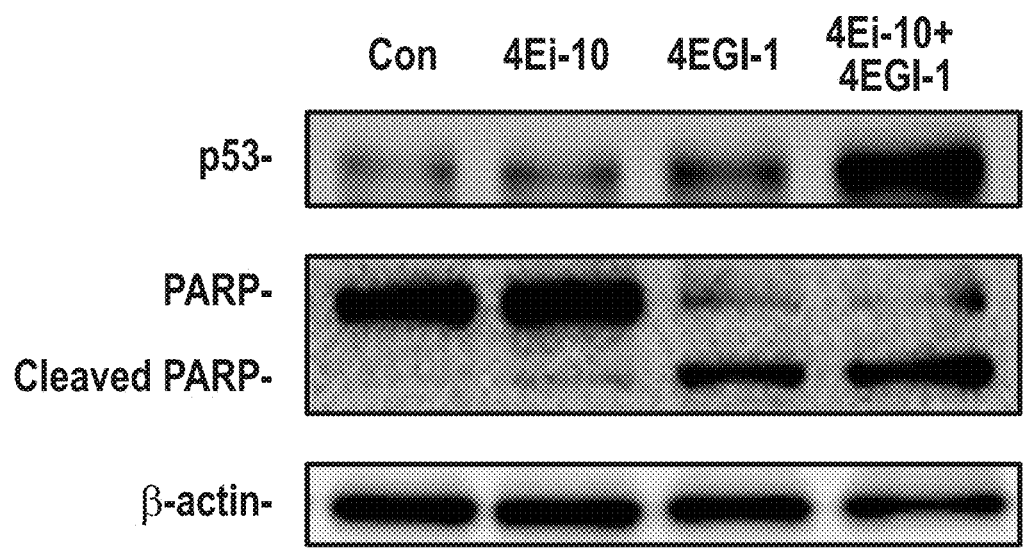
FIG. 3B is an immunoblot showing that 4Ei-10 and 4EGI-1 synergistically induces p53 and apoptosis in SH-SY5Y cells.

4EGI-1 is a small molecule that allosterically inhibits the interaction between eIF-4E and eIF-4G, preventing the formation of the eIF-4F complex without affecting 4E-BP1 binding. Recently, it was found that 4EGI-1 not only caused an increase in the p53 tumor suppressor protein concentration but also led to strong induction of apoptosis. Since both 4Ei-10 and 4EGI-1 can induce the p53 tumor suppressor protein in cancer cells through inhibition of cap-dependent protein translation, the capability of 4Ei-10 and 4EGI-1 in induction of the p53 tumor suppressor protein apoptosis was compared in SH-SY5Y cells. 4EGI-1 had a stronger ability in inducing the p53 tumor suppressor protein and apoptosis in SH-SY5Y cells than 4Ei-10 as shown in FIG. 3B. However, it was found that a much stronger increase in levels of the p53 tumor suppressor protein as well as in cellular apoptosis when SH-SY5Y cells were treated with both 4Ei-10 and 4EGI-1, compared to cells treated with 4Ei-10 or 4EGI-1 alone as shown in FIG. 3B. This result suggests that 4Ei-10 and 4EGI-1 may work synergistically to induce the p53 tumor suppressor protein and apoptosis in SH-SY5Y cells.

Example 6

Figure 4A:
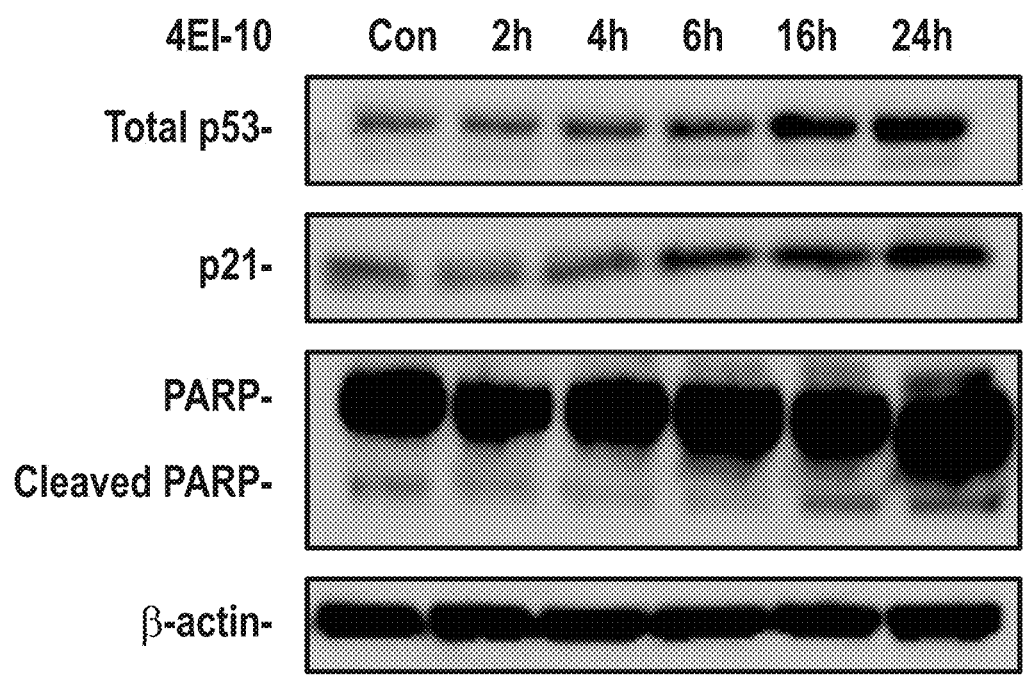
FIG. 4A is an immunoblot showing that 4Ei-10 induces p53 and its downstream events in CHLA-200, a pediatric glioblastoma multiforme cell line.

The ability of 4Ei-10 to induce the p53 tumor suppressor protein in other type of cell lines was also examined. CHLA-200 is a children's glioblastoma multiforme cell line with wild-type p53. CHLA-200 cells were treated with 100 µM 4Ei-10. Similar to SH-SY5Y cells, it was observed that 4Ei-10 induced p21Cip1 and PARP cleavage in CHLA-200 cells, indicating that 4Ei-10 induced both cell cycle arrest and apoptosis of CHLA-200 cells as shown in FIG. 4A.

Example 7

Figure 4B:
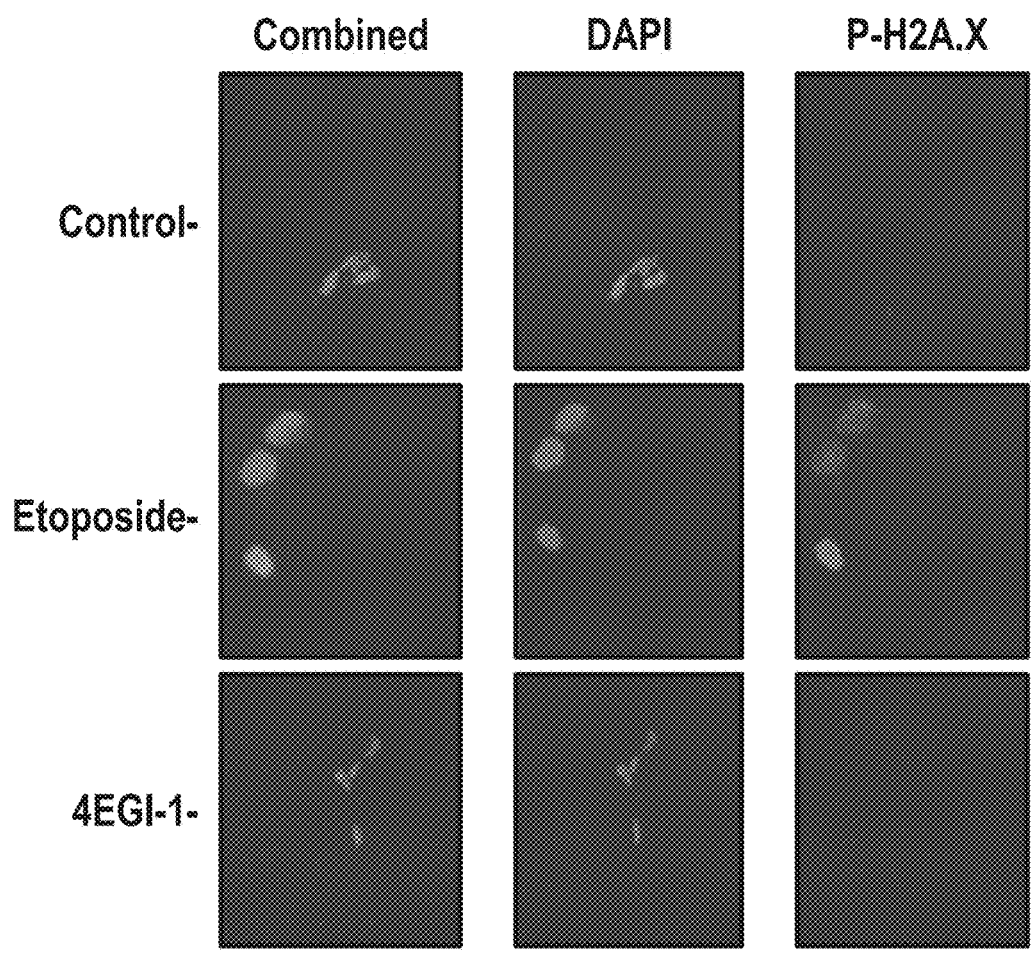
FIG. 4B is confocal microscope image showing that 4Ei-10 does not cause DNA double strand breaks in SH-SY5Y cells.

As most chemotherapeutic agents induce the p53 tumor suppressor protein by causing DNA damage, it was determined whether or not 4Ei-10 also induces DNA damage. Foci formation of phosphorylated H2A.X, which recognizes DNA double strand breaks, was examined. SH-SY5Y cells were treated with 4Ei-10 using etoposide as the positive control. While etoposide treatment induced the formation of a large amount of H2A.X foci within the nucleus of SH-SY5Y cells as shown in FIG. 4B, these foci were not seen in 4Ei-10-treated cells. These results indicate that 4Ei-10 is able to induce the p53 tumor suppressor protein without causing DNA double strand breaks in the cells.

Example 8

Figure 5A:
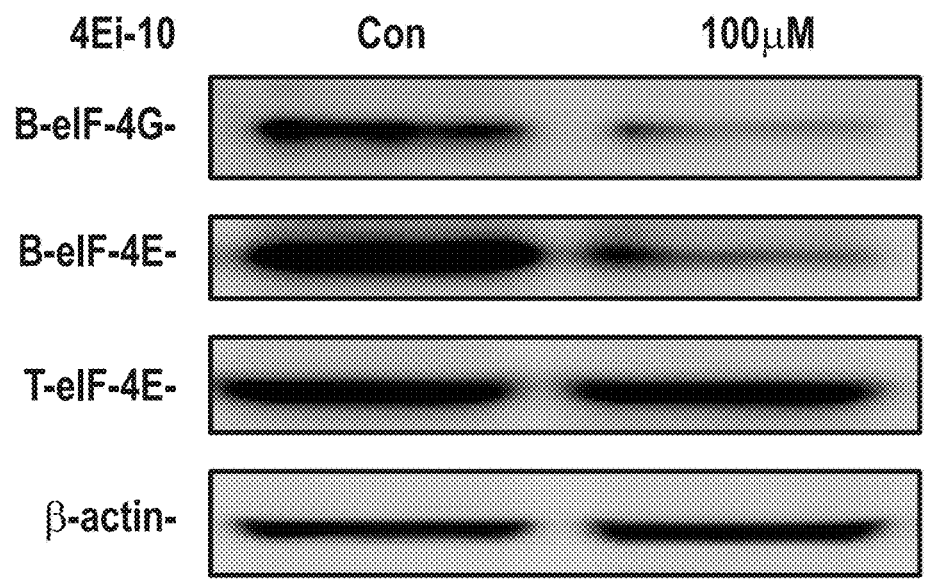
FIG. 5A is an immunoblot showing that 4Ei-10 treatment results in decreased eIF4E and eIF4G bound to the m7-GTP Sepharose beads.

SH-SY5Y cells were treated with 100 μM 4Ei-10 for 24 hours. After treatment, cells were lysed and equal amounts of proteins were incubated with $m^7$-GTP Sepharose beads. After incubation, beads were washed and mixed with SDS-PAGE loading buffer. The eluted proteins were then subjected to SDS-PAGE and transferred to a PVDF membrane. Bound eIF4G and eIF-4E were then detected with total eIF4E and total β-actin as input controls. The results shown in FIG. 5A demonstrate that 4Ei-10 treatment results in decreased eIF4E and eIF4G bound to the m7-GTP Sepharose beads.

Example 9

Figure 5B:
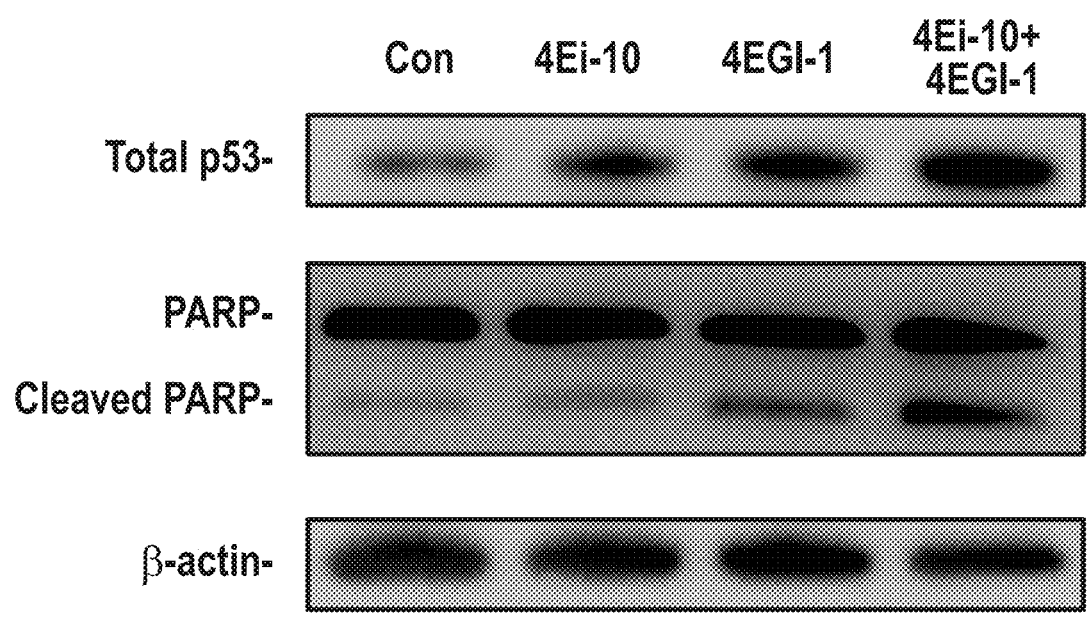
FIG. 5B is an immunoblot showing that 4Ei-10 and 4EGI-1 synergistically or additively induce p53 and apoptosis in MCF-7 cells.

Sub-confluent MCF-7 cells were treated with either 100 μM 4Ei-10, 50 μM 4EGI-1, or both for 24 hours. After treatment, both floating and attached cells were collected and lysed. Equal amounts of protein were subjected to SDS-PAGE and transferred to a PVDF membrane. p53, PARP, cleaved PARP, and β-actin were detected with their respective antibodies. The results shown in FIG. 5B demonstrate that 4Ei-10 and 4EGI-1 synergistically or additively induce p53 and apoptosis in MCF-7 cells.

The majority of current studies aimed at reactivating the p53 tumor suppressor protein in cancer cells retaining wild-type p53 have focused on inhibiting the interaction between MDM2 and the p53 tumor suppressor protein to increase the half-life of the protein. To date, these efforts have been met with only limited success. This is possibly due to the low frequencies of the MDM2 amplification in the majority of various types of cancer cells. In contrast, the results presented in the foregoing Examples provide a novel approach for stimulating the p53 tumor suppressor protein synthesis in cancer cells that harbor a wild-type p53 gene. It was found that 4Ei-10 causes increased synthesis of the p53 tumor suppressor protein, which in turn leads to the induction of cell cycle arrest and apoptosis in cancer cells that express wild-type p53. It was also shown that the induction of the p53 tumor suppressor protein is accompanied by enhanced IRES activity of p53 mRNA. Taken together, a novel mechanism to induce the p53 tumor suppressor protein in cancer cells by inhibiting cap-dependent translation and increasing IRES-mediated p53 tumor suppressor protein synthesis has been uncovered.

Cancer cells are "addicted" to growth factors and oncogenes such as cyclin D1 and c-myc. The mRNAs of these proteins contain "weak" 5'-untranslated regions (UTRs), which are long, complex structures that are not translated as efficiently as "strong" 5'-UTRs, which are relatively shorter, simpler structures. Because overexpression of eIF4E disproportionately upregulates oncogenes with complex 5'-UTRs relative to the less complex structures of housekeeping mRNAs, it is not surprising that cap-dependent inhibitors can specifically suppress the translation of multiple oncogenes and growth factors. This is supported by recent observations that eIF4E-haploinsufficient mice are physiologically normal yet resistant to tumor formation, suggesting that eIF4E dose is actually not a limiting factor for normal protein synthesis and cellular homeostasis, and high levels of eIF4E are critical for cancer development.

However, there is still no evidence to support the claim that inhibition of the translation of oncogenes and growth factors provides a mechanism leading to cell cycle arrest and/or apoptosis. As stated earlier, a switch from cap-dependent protein translation to IRES-mediated translation of p53 mRNA when cells are exposed to DNA damage was discovered. In addition, oncogene-induced senescence or OIS is a rapid cellular response that permanently shuts down further proliferation to prevent malignant transformation. It was also shown that cap-dependent protein translation switches to IRES-mediated cap-independent translation of p53 mRNA during OIS. The IRES of p53 mRNA exhibits enhanced activity following OIS, which leads to an increase in the p53 tumor suppressor protein accumulation as cap-dependent protein translation stops. In the present study, this switch has been further demonstrated in cancer cells treated with 4Ei-10, which induces IRES-mediated p53 tumor suppressor protein synthesis through inhibition of cap-dependent protein translation. This also provides an explanation as to why 4Ei-10 can induce cell cycle arrest and apoptosis while inhibiting cap-dependent protein translation.

DNA damaging agents, such as etoposide, are commonly used in cancer chemotherapy. However, these agents also cause serious collateral damage to benign cells, leading to increased risks of future cancer development in treated individuals. While the majority of traditional chemotherapeutic reagents trigger a p53 tumor suppressor protein response by inducing DNA damage (33), 4Ei-10, like 4EGI-1 (30), plays a similar role in induction of the p53 tumor suppressor protein without causing DNA double strand breaks. Therefore, it is conceivable that 4Ei-10 may replace some of the DNA damaging agents, thus preventing toxic side effects caused by traditional chemotherapy. Therefore, the capability of 4Ei-10 in inducing both cell cycle arrest and apoptosis not only makes 4Ei-10 a potent therapeutic agent for cancer treatment but may also allow it to be combined with DNA damaging agents, thereby decreasing cancer cells' drug resistance to traditional chemo- or radiation therapy.

More importantly, the effects of 4Ei-10 were tested on other cancer cell lines that still retain wild-type p53, including a pediatric glioblastoma multiforme cell line CHLA200 and an adult breast cancer cell line MCF-7. Induction of the p53 tumor suppressor protein was observed as well as increased cell apoptosis in both cell lines.

It should be noted that our previous results have shown that 4Ei-10 also inhibits cell proliferation and cell survival in multiple cell lines of mantle cell lymphoma (MCL). Furthermore, chemical inhibition of cap-dependent translation by 4Ei-10 results in suppression of c-Myc expression and enhanced chemosensitization to doxorubicin, dexamethasone, and ibrutinib. It was also shown that 4Ei-10 can induce the expression of p27, another G1 cell cycle regulator with known IRES structure at its 5'-UTR. See *J. Med. Chem.* 60: 8131-8144 (2017), which is incorporated by reference as if fully set forth herein. It should be noted that in this report (*J. Med. Chem.* 60: 8131-8144 (2017)), compound 6a is 4Ei-10. Compounds 6c (also known as 4Ei-11) and compound 7 are analogs of compound 6a, wherein X" represents a counterion:

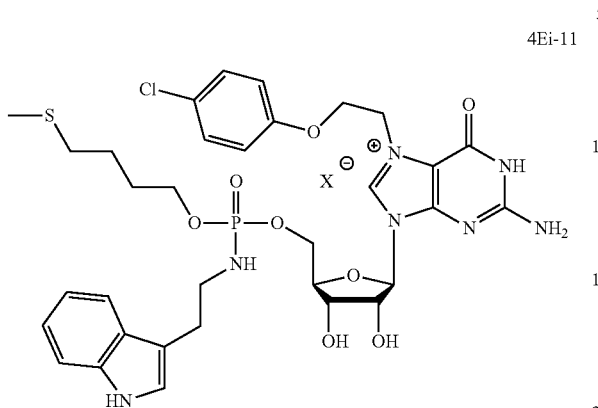

4Ei-11

In addition, 4Ei-10 exhibited a synergistic effect on the induction of the p53 tumor suppressor protein and apoptosis when combined with 4EGI-1, another cap dependent inhibitor that can induce the p53 tumor suppressor protein and apoptosis in cancer cells. These results suggest that strong inhibition of cap dependent protein translation might be a general mechanism for induction of the p53 tumor suppressor protein and its downstream events, and may lead to new efforts in searching for novel cap-dependent inhibitors as chemotherapeutic agents for cancer.

In addition to binding canonical initiation factors such as eIF4G, the IRES structure serves as an anchoring point for auxiliary protein initiation factors known as IRES transacting factors, or ITAFs. These ITAFs modulate activity of the IRES, either positively or negatively. Multiple ITAFs or putative ITAFs of the p53 mRNA IRES sequence have been identified and have been shown to either stimulate (positive ITAFs) or inhibit (negative ITAFs) synthesis of the p53 tumor suppressor protein. Furthermore, several proteins that can bind to the 3'-UTR of p53 mRNA and modulate its synthesis were also identified. Recently it was discovered that altered expression of ITAFs of p53 IRES is linked to defective the p53 tumor suppressor protein induction following DNA damage in cancer cells. It is thus conceivable that 4Ei-10 may reactivate the p53 tumor suppressor protein in cancer cell lines with wild-type p53 by modulating expression levels of the ITAFs of p53 IRES or regulatory proteins bound to p53 3'-UTR, which results in enhanced activity of p53 IRES and increased p53 tumor suppressor protein synthesis.

In summary, the findings in the foregoing Examples provide a mechanistic link between inhibition of cap-dependent protein translation by 4Ei-10 with enhanced the p53 tumor suppressor protein accumulation and increased cell cycle arrest and apoptosis in cancer cells. The ability of 4Ei-10, along with other cap-dependent inhibitors, to induce the p53 tumor suppressor protein and to specifically inhibit translation of oncogenic proteins makes these inhibitors a double-edged sword against cancer. While the detailed mechanism underlying 4Ei-10's role in inducing p53 tumor suppressor protein synthesis requires further investigation, the results described herein have introduced a new paradigm that links inhibition of cap-dependent protein translation with the p53 tumor suppressor protein induction, and may lead to the development of new treatment strategies and new therapeutic agents against cancer.

What is claimed is:

1. A compound of the formula (I):

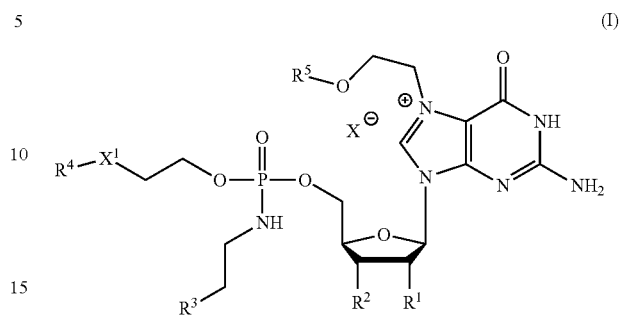

or a pharmaceutically acceptable salt thereof;
wherein:
$X^-$ represents a counterion;
$R^1$ and $R^2$ are each independently H, OH or alkoxy;
$R^3$ is alkyl, aryl or heterocyclyl;
$R^4$ is alkyl or aryl;
$R^5$ is aryl; and
$X^1$ is NH, S or O;
wherein the heterocyclyl is selected from the group consisting of piperidinyl, piperazinyl, morpholinyl, furanyl, pyrrolidinyl, pyridinyl, pyrazinyl, pyrimidinyl, triazinyl, thiophenyl, tetrahydrofuranyl, pyrrolyl, oxazolyl, imidazolyl, triazolyl, tetrazolyl, indolyl, benzoxazolinyl, and benzimidazolinyl groups.

2. The compound of claim 1, wherein the compound has the formula (II):

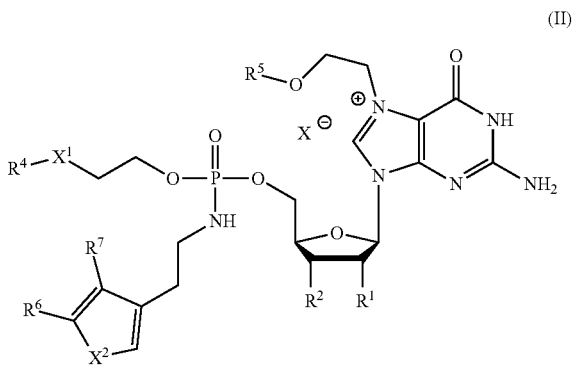

or a pharmaceutically acceptable salt thereof
wherein:
$X^-$ represents a counterion;
$R^1$ and $R^2$ are each independently H, OH or alkoxy;
$R^4$ is alkyl or aryl;
$R^5$ is aryl;
$X^1$ and $X^2$ are each independently NH, S or O;
$R^6$ and $R^7$ can each independently be H, alkyl, aryl or $R^6$ and $R^7$, together with the carbon atoms to which they are attached, form an aryl group selected from the group consisting of phenyl, napthalenyl, azulenyl, biphenylyl, indacenyl, fluorenyl, phenanthrenyl, triphenylenyl, pyrenyl, naphthacenyl, chrysenyl or anthracenyl.

3. The compound of claim 1, wherein the compound has the formula:

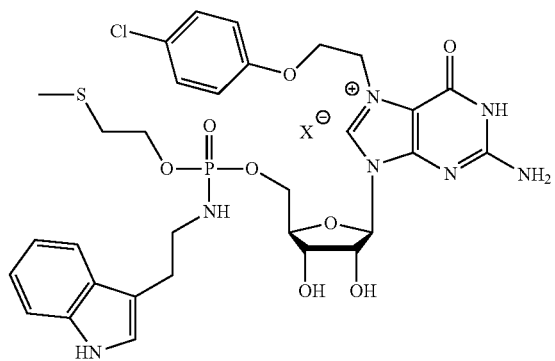

or a pharmaceutically acceptable salt thereof, wherein X⁻ represents a counterion.

4. The compound of claim 1, wherein the compound has the formula:

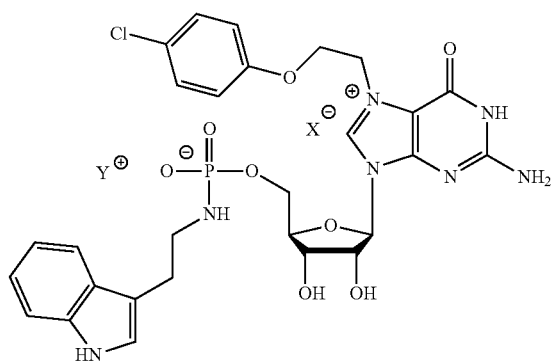

or a pharmaceutically acceptable salt thereof, wherein X⁻ and Y⁺ represent counterions.

5. A pharmaceutical composition comprising a compound of claim 1 and at least one pharmaceutically acceptable excipient.

6. A method for treating neuroblastoma, pediatric glioblastoma multiforme or breast cancer comprising administering a therapeutically effective amount of a compound of the formula:

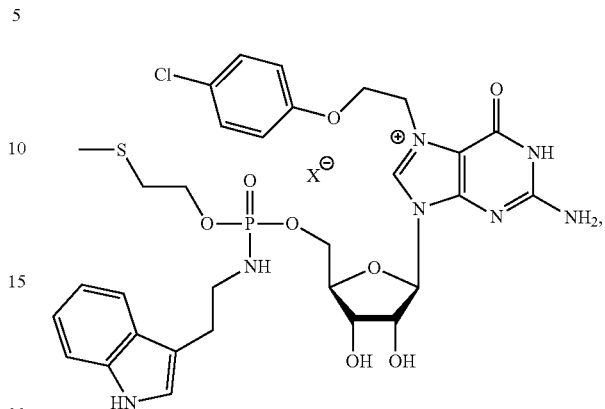

or a pharmaceutically acceptable salt thereof, wherein X⁻ represents a counterion, to a subject in need thereof.

7. A compound having the formula:

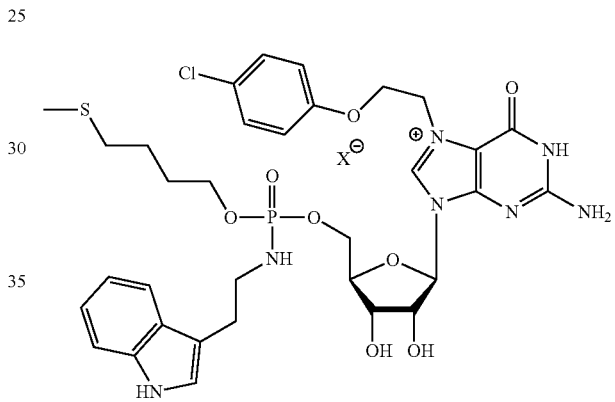

or a pharmaceutically acceptable salt thereof, wherein X⁻ represents a counterion.

* * * * *